(12) United States Patent
Chen et al.

(10) Patent No.: US 9,982,269 B2
(45) Date of Patent: *May 29, 2018

(54) MORTIERELLA ALPINE URACIL AUXOTROPH WITH URA5 GENE KNOCKED OUT THROUGH HOMOLOGOUS RECOMBINATION, AND CONSTRUCTION METHOD THEREOF

(71) Applicant: JIANGNAN UNIVERSITY, Wuxi (CN)

(72) Inventors: Wei Chen, Wuxi (CN); Haiqin Chen, Wuxi (CN); Yongquan Chen, Wuxi (CN); Guangfei Hao, Wuxi (CN); Zhennan Gu, Wuxi (CN); Jianxin Zhao, Wuxi (CN); Hao Zhang, Wuxi (CN); Xiaoyun Huang, Wuxi (CN); Kai Du, Wuxi (CN); Shanshan Zhao, Wuxi (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 31 days.

This patent is subject to a terminal disclaimer.

(21) Appl. No.: 14/910,675

(22) PCT Filed: Feb. 21, 2014

(86) PCT No.: PCT/CN2014/072350
§ 371 (c)(1),
(2) Date: Apr. 16, 2016

(87) PCT Pub. No.: WO2015/018198
PCT Pub. Date: Feb. 12, 2015

(65) Prior Publication Data
US 2016/0355831 A1 Dec. 8, 2016

(30) Foreign Application Priority Data
Aug. 9, 2013 (CN) .......................... 2013 1 0347934

(51) Int. Cl.
*C12N 15/80* (2006.01)
*C12N 9/10* (2006.01)

(52) U.S. Cl.
CPC .......... *C12N 15/80* (2013.01); *C12N 9/1077* (2013.01); *C12Y 204/0201* (2013.01)

(58) Field of Classification Search
None
See application file for complete search history.

(56) References Cited

U.S. PATENT DOCUMENTS

2007/0072275 A1* 3/2007 Ochiai .................. C12P 7/6463
435/134

OTHER PUBLICATIONS

Akcay et al. Plant Cell Reports (2009), 28(3), 407-417.*
Tsuji et al. Journal of General Plant Pathology (2003), 69(4), 230-239.*
Sugui et al. Appl Environ Microbiol. Apr. 2005; 71(4): 1798-1802.*
Takeno et al. Biosci Biotechnol Biochem. Feb. 2004;68(2):277-85.*
Bajpai et al. J Ind Microbiol. Oct. 1991;8(3):179-85.*

* cited by examiner

*Primary Examiner* — Christian Fronda
(74) *Attorney, Agent, or Firm* — CBM Patent Consulting, LLC (57) ABSTRACT

It relates to a *Mortierella alpine* ATCC32222 uracil auxotroph strain and a construction method thereof. In the present invention, *Mortierella alpine* ATCC32222 is used as a material and undergoes gene knockout through an *Agrobacterium tumefaciens* mediated genetic manipulation technology, to obtain the *Mortierella alpine* uracil auxotroph. The method is of great significance for the basic theoretic researches of the oil producing fungus *Mortierella alpine* ATCC32222 and product development.

1 Claim, 3 Drawing Sheets

MORTIERELLA ALPINE URACIL AUXOTROPH WITH URA5 GENE KNOCKED OUT THROUGH HOMOLOGOUS RECOMBINATION, AND CONSTRUCTION METHOD THEREOF

This application is the U.S. national phase of International Application No. PCT/CN2014/072350 Filed on 21 Feb. 2014 which designated the U.S. and claims priority to Chinese Application Nos. CN201310347934.8 filed on 9 Aug. 2013, the entire contents of each of which are hereby incorporated by reference.

FIELD OF THE INVENTION

The present invention relates to a *Mortierella alpina* uracil auxotrophic strain and its construction method. It is in the field of biotechnology engineering.

BACKGROUND OF THE INVENTION

*Mortierella alpina* is an important arachidonic acid (ARA) industrial production fungus. The produced polyunsaturated fatty acids (PUFAs) have a reasonable composition that contains high level of ARA, which have a record of complete safe for applications in food. By far, the studies on *M. alpina* were mainly focused on the strain breeding and the optimization of fermentation conditions. The gene transformation system of *M. alpina* has not been well established. This is a great obstacle to the studies on the mechanism of fatty acid synthesis and metabolic engineering of *M. alpina*. Auxotrophic marker, antibiotic resistance marker and fluorescent reporter gene are three well-used selective marker for gene transformation in filamentous fungi. The auxotrophic is applicable for industrial production, because there is no residual exogenous resistance gene. Therefore, the auxotrophic strains are important for industrial breeding microorganisms, genetics, medicine, food and biotechnology engineering. Currently, the auxotrophic strains of filamentous fungi are mainly generated by the mutation method, which is inefficient and often causes random unknown mutations in the genome DNA sequences. These unknown mutations may bring unpredictable problems for the future genetically engineering and industrial production.

Constructing auxotrophic through homologous recombination can knock out the target gene without affecting the function of the other genes. Compared to random mutations, homologous recombination is more efficient and repeatable. Therefore, directly interrupt the target gene via homologous recombination is an optional way in generating auxotrophic strains. In filamentous fungi, homologous recombination is affected by many factors: the length, similarity, G/C percentage, transcription of target gene, non-homologous end joining and chromatin structure, as well as the transformation method. In some yeast, homologous recombination could be achieved with a relative short homologous DNA sequence of 50 bp to 100 bp. Whereas in filamentous fungi, homologous DNA sequence often needs to be over 1K bp even longer. The homologous recombination probability may differ a lot among strains and genes, which may strongly affect the experiment. Orotate phosphoribosyltransferase (OPRTase) is a key enzyme during uracil metabolic in *M. alpina*. The *M. alpina* auxotroph could be generated by inactivation the OPRTase coding gene ura5. However, ura5 gene has an extremely important role in the cellular processes of life, resulting in very sensitive self-defense and repair mechanisms of the role of eukaryotic cells. Construction of ura5 uracil auxotrophic strain using gene knockout method in filamentous fungi is seldom publicly reported.

The gene manipulation system of filamentous fungus has not been well established, mainly because it is difficult to be transformed. *Agrobacterium tumefaciens*-mediated transformation (ATMT) method has been gradually applied in filamentous fungi, which have four advantages compared to other transformation methods. First, the recipient could be spores or mycelia without preparing protoplasts. Second, the mononuclear spores as a recipient can avoid transformants instability caused by multicore mycelium. Third, the method uses a natural transformation vector system having high conversion efficiency and high success rate. The plasmid can hold large fragments of DNA with a single copy insertion into genome. Fourth, a relative higher homologous recombination rate can be achieved.

The *M. alpina* uracil auxotrophic strain is the prerequisites of the gene manipulation of this important industrial PUFA production fungus. This uracil auxotrophic strain could be applied in both theoretical research of fatty acid synthesis and accumulation and genetically engineering to breeding super PUFA production industrial strain.

SUMMARY OF THE INVENTION

The object of the present invention is to provide a uracil auxotrophic strain of *M. alpina*. The auxotroph was constructed by deletion of the 18 bp (213 bp to 230 bp) of the *M. alpina* ATCC 32222 ura5 gene (654 bp).

The sequence of the homologous DNA arms refers to the 1393 bp (from −1180 bp to +212 bp) up-stream and the 1362 bp (from +231 bp to +1592 bp) down-stream of the ura5 gene of *M. alpina* ATCC 3222 genome sequence (DDBJ/EMBL/GenBank accession ADAG00000000, first version ADAG01000000).

Figure 1:
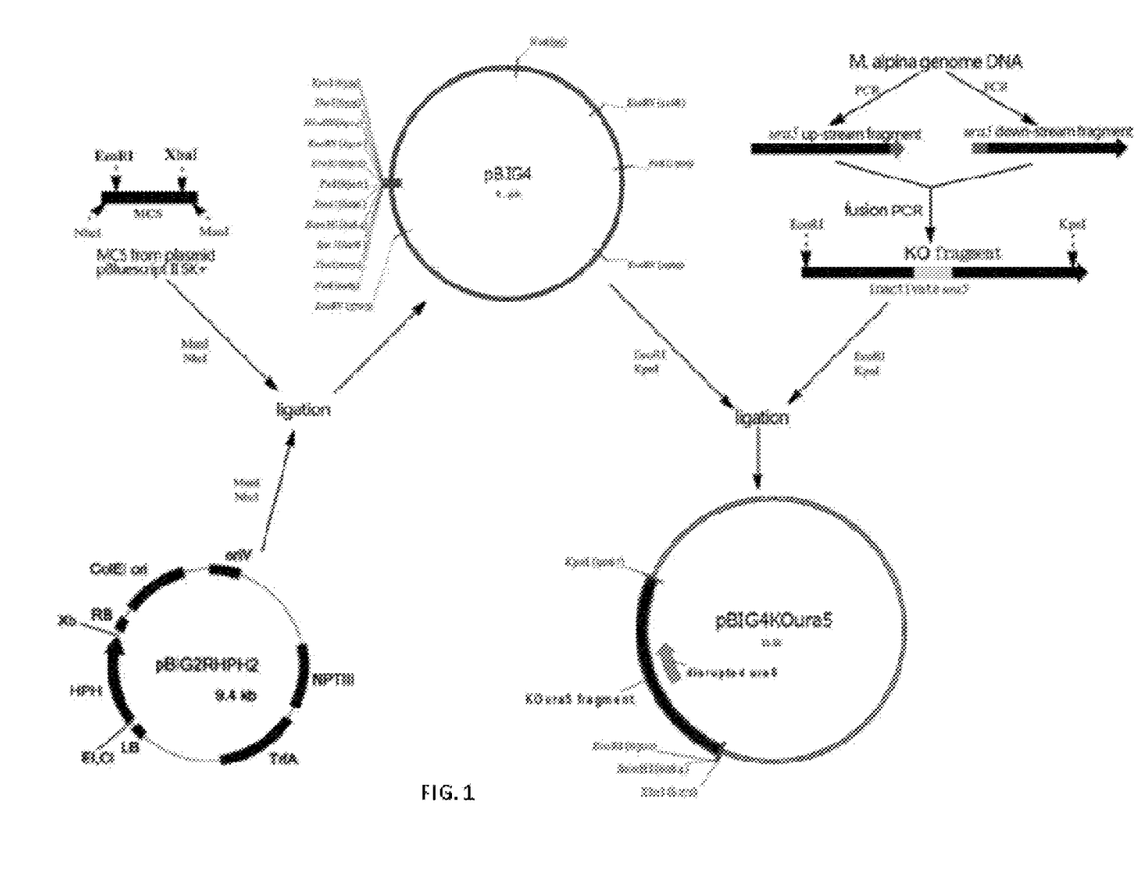
FIG. 1 is the schematic diagram of the construction of the plasmid for gene knockout.
Figure 2:
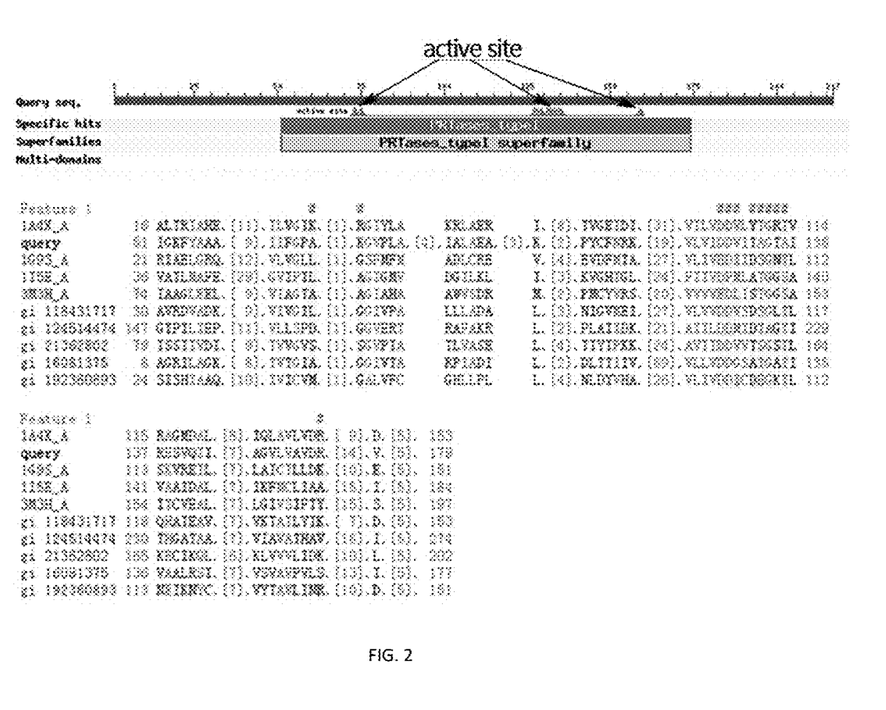
FIG. 2 is the analysis diagram of the conserved region of *M. alpina* OPRTase.

The present invention also provides a method of constructing the uracil auxotrophic strain of *M. alpina* comprising: obtaining the ura5 knockout DNA fragment; constructing the knockout plasmid pBIG4KOura5; transformation of *A. tumefaciens* using pBIG4KOura5; ATMT of *M. alpina* using *A. tumefaciens* that containing pBIG4KOura5; screening and identifying uracil auxotroph to obtain uracil auxotrophic strains. As illustrated in FIG. 1, the multiple cloning site (MCS) DNA fragment is PCR amplified from plasmid pBluescript II SK+. Digest the MCS fragment and plasmid pBIG2RHPH2 with NheI/MunI and EcoRI/XbaI, followed by the ligation to form plasmid pBIG4. Ligate the up- and down-stream knockout DNA arms with fusion PCR to form the knockout DNA fragment KOura5. Digest the KOura5 fragment and plasmid pBIG4, followed by the ligation to form plasmid pBIG4KOura5. Transform *A. tumefaciens* C58C1 using plasmid pBIG4KOura5. ATMT *M. alpina* disrupts the ura5 gene to construct uracil auxotrophic strain of *M. alpina*.

Specifically, this invention provides a *M. alpina* uracil auxotrophic strain, which is generated by inactivating the ura5 encoding orotate phosphoribosyltransferase (OPRTase).

According to one preferable embodiment of the present invention, the inactivation of the 654 bp ura5 gene is achieved by the deletion of the 18 bp (213 bp to 230 bp) DNA sequence.

The present invention also provides a method for the construction of *M. alpina* uracil auxotroph according to any of claims 1 and 2. Inactivate the *M. alpina* ura5 gene through deletion of the 18 bp (213 bp to 230 bp) DNA sequence by homologous recombination. The homologous DNA arms are the 1393 bp (from −1180 bp to +212 bp) up-stream and the 1362 bp (from +231 bp to +1592 bp) down-stream of the ura5 gene. The detailed steps are described as follows: obtaining the ura5 knockout DNA fragment; constructing the knockout plasmid pBIG4KOura5; transformation of *A. tumefaciens* using pBIG4KOura5; ATMT of *M. alpina* using *A. tumefaciens* C58C1-pBIG4KOura5 (CGMCC No. 7730); screening and identifying uracil auxotroph to obtain uracil auxotrophic strains.

In the present invention, the *A. tumefaciens* used is *Agrobacterium tumefaciens* C58C1, received from Professor Yasuyuki Kubo (Kyoto Prefectural University, Kyoto, Japan).

The starting *A. tumefaciens* plasmid is pBIG2RHPH2, received from Professor Yasuyuki Kubo (Kyoto Prefectural University, Kyoto, Japan), with sequence of SEQ No. 1.

According to a preferable embodiment of the present invention, the gene knockout plasmid is constructed as follows:

(a) amplifying the MCS DNA fragment is by PCR using plasmid pBluescript II SK+ as template;

(b) digesting MCS DNA fragment and plasmid pBIG2RHPH2 by EcoRI and XbaI, and ligating them together at the EcoRI and XbaI sites to form the plasmid pBIG4;

(c) PCR amplifying the up- and down-stream arms of ura5 gene and ligating them together by using fusion PCR to form knockout DNA sequence;

(d) digesting the KOura5 knockout DNA sequence and pBIG4 by EcoRI and KpnI, and ligating them together to form plasmid pBIG4KOura5.

Preferably, the knockout DNA sequence in step (c) is constructed as the following steps:

designing the primers according to the sequence data of NCBI:

P1:
GACCGGAATTCCGACGCTGACATTACACATTTATCC

P2:
TGACGGTGGTGCAGGCCAGAGGGCCAAAGATGATGTCGTGCTCAATG

P3:
TTGAGCACGACATCATCTTTGGCCCTCTGGCCTGCACCACCGTCATT

P4:
TGCGGGGTACCCATGCGAATCACAGATATGG subsequently, PCR amplifying up- and down-stream DNA fragments by using P1/P2 and P3/P4 with *M. alpina* ATCC 32222 genome DNA as template, then performing fusion PCR by using P1/P4 with up- and down-stream DNA fragments as templates to amplify the KOura5 knockout DNA sequence.

More preferably, the primers below are designed according to the sequence of pBluescript II SK+:

MCSF:
TTTCGCTAGCACGACGTTGTAAAACGACGGCCAGT

MCSR:
AACAACAATTGGGGCTCCACCGCGGTGGCGGCCG

Then the MCS DNA fragment in step (a) is amplified by PCR using primer pair MCSF/MCSR with pBluescript II SK+ as template.

The said ATMT gene knockout consists in using *A. tumefaciens* to transform *M. alpina*, specified as follows: mixing equal volume of 100 μL of *A. tumefaciens* and *M. alpina* spores, and spreading on the cellophane membrane placed on the IM solid medium, after co-cultivation, selecting the uracil auxotrophic strains of *M. alpina*.

The ATMT method comprises:

(i) separating the *A. tumefaciens* harboring pBIG4KOura5 (preserved at the temperature of −80° C.) by stripping on the TEP solid plate (containing 100 μg/mL rifampicin and 100 μg/mL kanamycin) to obtain single clone by cultured at the temperature of 30° C. for 48 h.

(ii)(2) transferring a single clone to 20 mL YEP medium (containing 100 μg/mL rifampicin and 100 μg/mL kanamycin) and culturing at the temperature of 30° C. for 48 h with shaking at 200 rpm in the dark;

(iii) collecting *A. tumefaciens* by centrifuging at 4000×g for 5 min, after removing the suspension, suspending the pellet by 5 mL of IM medium, followed by a centrifugation at 4000×g for 5 min, and then removing the suspension, adding 2 mL of IM medium to suspend the bacterium;

(iv) adjusting the concentration of the bacterium suspension to OD600=0.9, followed by a dark cultivation at the temperature of 30° C. to OD600=1.5;

(v) collecting the *M. alpina* spores, counting the number, then adjusting the spore concentration to $10^6/100$ μL;

(vi) mixingequal volume of 100 μL of *A. tumefaciens* and spores, spreading on the cellophane membrane placed on the IM solid medium, then incubating at the temperature of 23° C. for 48 to 96 h in a dark incubator;

(vii) transferring the cellophane membrane onto GY plate containing 100 μg/mL cefotaxime and 100 μg/mL spectinomycin, then incubating at the temperature of 25° C. to 30° C. until spores appears.

In this invention, the IM solid medium is composed of 1.74 g/L $K_2HPO_4$, 1.37 g/L $KH_2PO_4$, 0.146 g/L NaCl, 0.49 g/L $MgSO_4 \cdot 7H_2O$, 0.078 g/L $CaCl_2$, 0.0025 g/L $FeSO_4 \cdot 7H_2O$, 0.53 g/L $(NH_4)_2SO_4$, 7.8 g/L MES, 1.8 g/L glucose, 0.5% glycerol and 20 g/L agar.

The present invention builds a *M. alpina* uracil auxotrophic strain using the ATMT gene knockout method, based on the bioinformatics analysis of *M. alpina* ATCC 32222 genome, after a lot of practice. The *M. alpina* uracil auxotrophic strain has genetic stability after several generations, and fatty acid composition shows no significant difference with the wild-type strain. This uracil auxotroph can be used as a recipient strain for genetic engineering.

The *A. tumefaciens* C58C1-pBIG4KOura5 obtained according to this invention was preserved in China General Microbiological Culture Collection Center (CGMCC) since Jun. 28, 2013, with the accession number CGMCC No. 7730. The address of CGMCC is the Institute of Microbiology, Chinese Academy of Sciences, No. 1, Beichen West Road, Chaoyang District, Beijing, China, Zip code 100101.

EMBODIMENTS

The following Embodiments further illustrate the present invention. The experimental methods without indicating specific conditions in the following examples will be performed generally in accordance with the manual of molecular cloning experiments.

Example 1: The Bioinformatics Analysis of *M. alpina* Genome

Compare the protein coding sequence, which was predicted based on the *M. alpina* ATCC 32222 genome (DDBJ/EMBL/GenBank accession ADAG00000000, first version ADAG01000000), to the database NR (www.ncbi.nlm.nih.gov), KOGs and COGs, KEGG, Swiss-Prot, UniRef100, and BRENDA using BLAST (E-value 1E-5). Search InterProScan against protein domain databases with default parameter settings. Predict the 654 bp ura5 gene coding sequence and find no intron exists. Search the *M. alpina* genome sequence with the sequence of ura5 gene for the up- and down-stream sequence.

Example 2: Obtaining the KOura5 DNA Fragment

Find the conserved active site of the protein sequence of *M. alpina* OPRTase (FIG. 1). Design different homologous arms to disrupt ura5 gene. After many practice and comparison of the different plans, confirm that the effective homologous DNA arms are the 1393 bp (from −1180 bp to +212 bp) up-stream and the 1362 bp (from +231 bp to +1592 bp) down-stream of the ura5 gene. The details of the success experimental plan are as follows:

First, design primers based on the bioinformatics analysis.

```
P1:
GACCGGAATTCCGACGCTGACATTACACATTTATCC

P2:
TGACGGTGGTGCAGGCCAGAGGGCCAAAGATGATGTCGTGCTCAATG

P3:
TTGAGCACGACATCATCTTTGGCCCTCTGGCCTGCACCACCGTCATT

P4:
TGCGGGGTACCCATGCGAATCACAGATATGG
```

Figure 3:
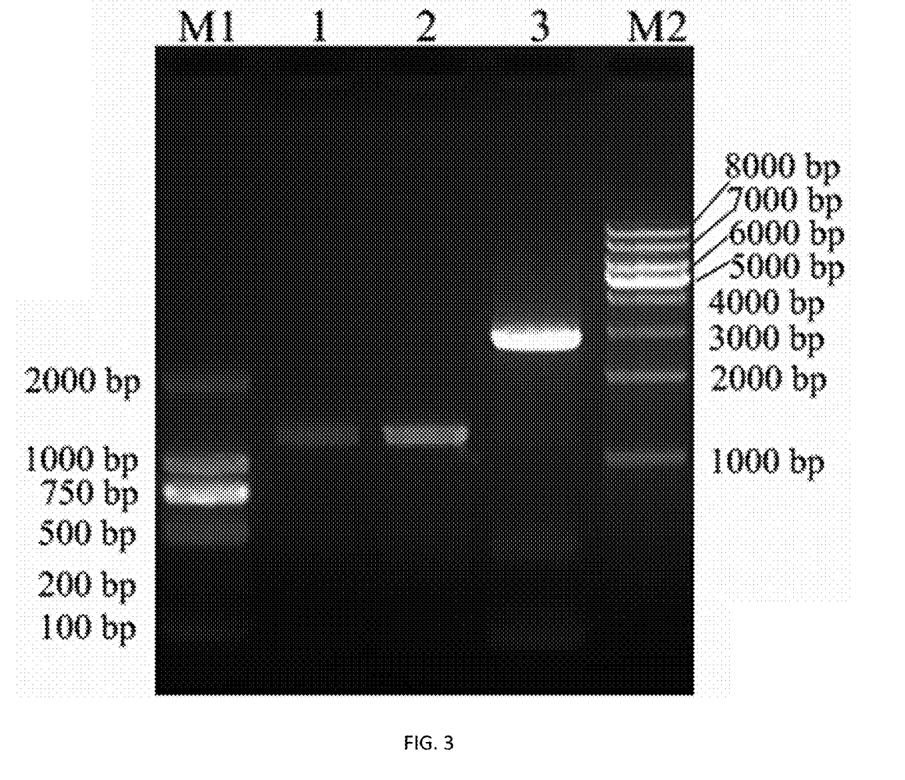
FIG. 3 is the agarose gel electrophoresis of the fusion PCR fragments.

Introduce EcoRI and KpnI into the 5' site of P1 and P4. PCR amplify the up- and down-stream fragments of ura5 gene with *M. alpina* genome as template, followed by a gel purification. Ligate the two fragments using fusion PCR with primer pair P1/P4 using the up- and down-stream fragments as templates. FIG. 3 is the results of the agarose gel. As shown in the picture, M1 is the D2000 Marker; channel 1 is the up-stream fragment; channel 2 is the down-stream fragment; channel 3 is the fusion PCR product; M2 is the 1 kb ladder Marker. Sub-clone the fragment of fusion PCR into the pEGMT-easy vector and analyze the sequence by ABI PRISM 3730.

Example 3: Construction of the Knockout Plasmid pBIG4KOura5

Design primers according to the sequence of plasmid pBluescript II SK+:

```
MCS Forward:
TTTCGCTAGCACGACGTTGTAAAACGACGGCCAGT

MCS Reverse:
AACAACAATTGGGGCTCCACCGCGGTGGCGGCCG
```

MCS DNA fragment was amplified from plasmid pBluescript II SK+.

Digest the MCS fragment and plasmid pBIG2RHPH2 with EcoRI and XbaI, followed by a gel purification and ligation. The 10 μL ligation mixtures consisted of: MCS DNA fragment 2 μL, plasmid 2 μL, 10×T4 ligase buffer 1 μL, T4 ligase 1 μL and $H_2O$ 4 μL. Ligate at the temperature of 4° C. for 12 h.

Directly transform the ligation product into *Escherichia coli* TOP10 competent cell. The electro transformation comprises:

(a) Take out 100 μL competent cells under sterile conditions, add 1 to 2 μL ligation product and mix.

(b) Transfer the mixture of step (a)(1) into cuvette, avoiding to make air bubbles.

(c) Transfer the cuvette into the Bio-Rad electroporation device, select the appropriate program and click pulse.

(d) Transfer the pulsed competent cell into 900 μL SOC medium and incubate at the temperature of 37° C. at 150 rpm for 1 h.

(e) Transfer 200 μL of the culture onto YEP plate (containing 100 μg/mL kanamycin) and spread with a sterile stick. Inverted incubate overnight at the temperature of 37° C.

Select the positive transformants and extract the plasmid. Analyze the sequence by ABI PRISM 3730. The resulted plasmid is named as pBIG4.

Digest KOura5 DNA fragment and plasmid pBIG4 with Nhe/MunI and EcoRI/KpnI, followed by the gel purification and ligation. Ligate with the ligase T4. Transform the reaction mixture into TOP10 competent, select positive clone and analysis of the DNA sequence proves ligation successful. The resulted plasmid is named as pBIG4KOura5.

The SOC medium was composed of 20 g/L Tryptone, 5 g/L yeast extract, 0.5 g/L NaCl, 2.5 mM KCl, 10 mM $MgCl_2$ and 20 mM glucose; The YEP solid medium was composed of 10 g/L Tryptone, 10 g/L yeast extract, 5 g/L NaCl and 20 g/L agar.

Example 4: ATMT of *M. alpina*

The transformation was optimized according to the method referred to the open accessed articles, the detailed steps are as follows:

(i) Take out the *A. tumefaciens* C58C1 (harboring pBIG4KOura5) preserved at the temperature of −80° C. and separate by stripping on the TEP solid plate (containing 100 μg/mL rifampicin and 100 μg/mL kanamycin) to obtain single clone by cultured at the temperature of 30° C. for 48 h.

(ii) Transfer a single clone to 20 mL YEP medium (containing 100 μg/mL rifampicin and 100 μg/mL kanamycin) and cultured at the temperature of 30° C. for 48 h with shaking at 200 rpm in the dark.

(iii) Collect *A. tumefaciens* by centrifuging at 4000×g for 5 min. After remove the suspension, suspend pellet by 5 mL of IM medium, followed by a centrifugation at 4000×g for 5 min. After remove the suspension, add 2 mL of IM medium to suspend the bacterium.

(iv) Adjust the concentration of the bacterium suspension to OD600=0.9, followed by a dark cultivation at the temperature of 30° C. to OD600=1.5;

(v) Collect the *M. alpina* spores and count the number, then adjust the spore concentration to $10^6$/100 μL;

(vi) Mix equal volume of 100 μL of *A. tumefaciens* and spores and spread on the cellophane membrane placed on the IM solid medium, then incubate at the temperature of 23° C. for 48 to 96 h in a dark incubator;

(vii) Transfer the cellophane membrane onto GY plate containing 100 μg/mL cefotaxime, 100 μg/mL spectinomycin and 0.05 g/L uracil, then incubate at the temperature of 25° C. to 30° C. until spores appears.

Wherein, the liquid YEP medium was composed of 10 g/L Tryptone, 10 g/L yeast extract and 5 g/L NaCl.

Example 5: Screening and Identification of *M. alpina* Uracil Auxotroph (a) Scour the surface of the co-cultured template with 3 mL of saline solution. Collecte the solution with 1.5 mL tube and filter with 25 μm membrane.

(b) Spread 200 μL of the solution onto GY plate (containing 1 mg/mL 5-FOA, 100 μg/mL spectinomycin, 100 μg/mL cefotaxime and 0.05 g/L uracil).

(c) Incubate the plate at the temperature of 25° C. for 5 to 10 days in the dark.

(d) Transfer the visible mycelium onto GY plate (containing 1 mg/mL 5-FOA, 100 μg/mL spectinomycin, 100 μg/mL cefotaxime and 0.05 g/L uracil), and cultivate at the temperature of 25° C. for 2 to 4 days in a dark incubator.

(e) Transfer the well grown mycelium in step (d) separately onto the SC plate containing uracil and the SC plate without uracil. Cultivate at the temperature of 25° C. for 2 to 4 days.

(f) Observe the growth of the mycelium on the two SC plates. Select the mycelium only grown on the SC plate containing uracil and then transfer them onto the GY medium slant containing 0.5 mg/mL 5-FOA.

(g) Culture the *M. alpina* spores of step (f) for 3 generations on GY medium slant containing 0.5 mg/mL 5-FOA. Repeat the experiment described in step (e) each generation.

(h) Identify the genetic stable strains as uracil auxotrophic phenotype and preserve on GY medium slant containing 0.5 mg/mL 5-FOA.

(i) Extract the genome of the uracil auxotroph and PCR for ura5 gene with the primers below:

```
Forward:
ATGACCATCAAGGATTACCAGCGCG

Reverse:
ATCCTTAAACACCGTACTTCTCGCG
```

Purify the PCR product and analyze sequence by ABI PRISM 3730. Identify the gene as loss of 213 bp to 230 bp.

Example 6: Extraction and Analysis of the Fatty Acids of *M. alpina* Uracil Auxotroph (a) Culture the *M. alpina* prototrophic strain and three *M. alpina* uracil auxotroph strains screened in Example 5 in ferment medium (adding extra 0.05 g/L uracil for auxotroph strains) at the temperature of 25° C. at 200 rpm for 7 to 14 days.

Wherein, the ferment medium is available on the market, and is composed of 50 g/L glucose, 2.0 g/L L-Ammonium tartrate, 7.0 g/L $KH_2PO_4$, 2.0 g/L $Na_2HPO_4$, 1.5 g/L $MgSO_4 \cdot 7H_2O$, 1.5 g/L Yeast extract, 0.1 g/L $CaCl_2 \cdot 2H_2O$, 8 mg/L $FeCl_3 \cdot 6H_2O$, 1 mg/L $ZnSO_4 \cdot 7H_2O$, 0.1 mg/L $CuSO_4 \cdot 5H_2O$, 0.1 mg/L $Co(NO_3)_2 \cdot 6H_2O$ and 0.1 mg/L $MnSO_4 \cdot 5H_2O$.

(b) Collect mycelia and freeze-dry.

(c) Mix 100 mg mycelia (dry weight) with 2 mL of 4 mol/L HCl.

(d) Water bath at 80° C. for 0.5 h, then at −80° C. for 15 min. Repeat once. Then water bath at 80° C. for 0.5 h.

(e) Cool down the mixture to room temperature, add 1 mL methanol and well mix.

(f) Add 1 mL chloroform and shake for 10 min, followed by centrifuge at 6000×g for 3 min. Collect the chloroform.

(g) Repeat step (f) for two times.

(h) Combine chloroform (3 mL), add 1 mL saturated NaCl solution, mix well and centrifuge at 3000×g for 3 min. Transfer the chloroform into a new tube. Add 1 mL chloroform in the residual liquid, followed by centrifugation at 3000×g for 3 min. Combine all the chloroform (4 mL)

(i) After drying by nitrogen blow, add 1 mL ethyl ether. Transfer the solution to a clean and weighed tube, followed by drying by nitrogen blow, then weigh it to obtain total fatty acid weight. The total fatty acid content of prototrophic and three uracil auxotroph *M. alpina* are listed in Table 1.

TABLE 1

The total fatty acid of prototrophic and three uracil auxotroph *M. alpina*

| Strains | Dry Weight (mg) | Fatty Acid Content (%) |
|---|---|---|
| MA | 46.2 | 30.64 ± 0.035 |
| MAU1 | 49.0 | 30.56 ± 0.026 |
| MAU2 | 50.5 | 30.72 ± 0.036 |
| MAU3 | 52.1 | 30.60 ± 0.029 |

(j) Analyze the fatty acids by GC

The total fatty acid composition of prototrophic and three uracil auxotroph *M. alpina* are listed in Table 2.

TABLE 2

The total fatty acid composition of prototrophic and three uracil auxotroph *M. alpina*

| Strains | Fatty Acid Composition (%) | | | | | | | | |
|---|---|---|---|---|---|---|---|---|---|
| | 16:0 | 18:0 | 18:1 | 18:2 | 18:3 | 20:3 | 20:4 | 22:0 | 24:0 |
| MA | 14.98 | 10.73 | 8.91 | 15.60 | 2.61 | 1.97 | 34.53 | 1.27 | 1.79 |
| MAU1 | 13.59 | 10.98 | 9.40 | 17.17 | 2.59 | 1.81 | 34.50 | 1.21 | 1.57 |
| MAU2 | 14.4 | 11.35 | 9.67 | 16.83 | 2.56 | 1.90 | 34.84 | 1.26 | 1.62 |
| MAU3 | 13.56 | 10.48 | 9.17 | 16.43 | 2.43 | 1.66 | 34.16 | 1.20 | 1.54 |

The results of experiments show that the uracil auxotrophic *M. alpina* that constructed according to the method of the experiments has genetic stability after cultured for multiple generations, and its fatty acid analysis shows no distinguished difference between that of prototrophic *M. alpina* strains. The strain constructed according to the method of the present invention could be taken as the recipient strain for genetic engineering.

Above-mentioned preferred embodiments are not intended to limit the present invention. Those skilled in the art, without departing from the spirit and scope of the present invention, can make a variety of variations and modifications. Therefore, the protection scope of the present invention shall be based on the claims.

What is claimed is:

1. An isolated *Mortierella alpina* MAU1 deposited at the General Microbiology Culture Collection Center of China Committee for Culture Collection of Microorganisms under accession number CGMCC No. 8414.

* * * * *

UNITED STATES PATENT AND TRADEMARK OFFICE
CERTIFICATE OF CORRECTION

PATENT NO. : 9,982,269 B2
APPLICATION NO. : 14/910675
DATED : May 29, 2018
INVENTOR(S) : Wei Chen et al.

Page 1 of 1

It is certified that error appears in the above-identified patent and that said Letters Patent is hereby corrected as shown below:

On the Title Page

Item (54) and in the Specification, Column 1, Lines 1-5 the title should read as:
*MORTIERELLA ALPINA* URACIL AUXOTROPH WITH URA5 GENE KNOCKED OUT THROUGH HOMOLOGOUS RECOMBINATION, AND CONSTRUCTION METHOD THEREOF Item (57) ABSTRACT should read as:
It relates to a *Mortierella alpina* ATCC32222 uracil auxotroph strain and a construction method thereof. In the present invention, *Mortierella alpina* ATCC32222 is used as a material and undergoes gene knockout through an *Agrobacterium tumefaciens* mediated genetic manipulation technology, to obtain the *Mortierella alpina* uracil auxotroph. The method is of great significance for the basic theoretic researches of the oil producing fungus *Mortierella alpina* ATCC32222 and product development.

Signed and Sealed this
Twenty-third Day of October, 2018

Andrei Iancu
*Director of the United States Patent and Trademark Office*

SEQUENCE LISTING

<160> NUMBER OF SEQ ID NOS: 12

<210> SEQ ID NO 1
<211> LENGTH: 9666
<212> TYPE: DNA
<213> ORGANISM: Unknown
<220> FEATURE:
<223> OTHER INFORMATION: It is a comercial plasmid named as pBIG2RHPH2

<400> SEQUENCE: 1

| | | | | | |
|---|---|---|---|---|---|
| ccgggctggt | tgccctcgcc | gctgggctgg | cggccgtcta | tggccctgca | aacgcgccag | 60 |
| aaacgccgtc | gaagccgtgt | gcgagacacc | gcggccgccg | gcgttgtgga | tacctcgcgg | 120 |
| aaaacttggc | cctcactgac | agatgagggg | cggacgttga | cacttgaggg | gccgactcac | 180 |
| ccggcgcggc | gttgacagat | gaggggcagg | ctcgatttcg | gccggcgacg | tggagctggc | 240 |
| cagcctcgca | aatcggcgaa | aacgcctgat | tttacgcgag | tttcccacag | atgatgtgga | 300 |
| caagcctggg | gataagtgcc | ctgcggtatt | gacacttgag | gggcgcgact | actgacagat | 360 |
| gaggggcgcg | atccttgaca | cttgaggggc | agagtgctga | cagatgaggg | gcgcacctat | 420 |
| tgacatttga | ggggctgtcc | acaggcagaa | aatccagcat | ttgcaagggt | ttccgcccgt | 480 |
| ttttcggcca | ccgctaacct | gtcttttaac | ctgcttttaa | accaatattt | ataaaccttg | 540 |
| tttttaacca | gggctgcgcc | ctgtgcgcgt | gaccgcgcac | gccgaagggg | ggtgccccc | 600 |
| cttctcgaac | cctcccggcc | cgctaacgcg | ggcctcccat | cccccaggg | gctgcgcccc | 660 |
| tcggccgcga | acgcctcac | cccaaaaatg | gcagcgctgg | cagtccttgc | cattgccggg | 720 |
| atcggggcag | taacgggatg | ggcgatcagc | ccgagcgcga | cgcccggaag | cattgacgtg | 780 |
| ccgcaggtgc | tggcatcgac | attcagcgac | caggtgccgg | gcagtgaggg | cggcggcctg | 840 |
| ggtggcggcc | tgcccttcac | ttcggccgtc | ggggcattca | cggacttcat | ggcggggccg | 900 |
| gcaatttta | ccttgggcat | tcttggcata | gtggtcgcgg | gtgccgtgct | cgtgttcggg | 960 |
| ggtgcgataa | acccagcgaa | ccatttgagg | tgataggtaa | gattataccg | aggtatgaaa | 1020 |
| acgagaattg | gacctttaca | gaattactct | atgaagcgcc | atatttaaaa | agctaccaag | 1080 |
| acgaagagga | tgaagaggat | gaggaggcag | attgccttga | atatattgac | aatactgata | 1140 |
| agataatata | tcttttatat | agaagatatc | gccgtatgta | aggatttcag | ggggcaaggc | 1200 |
| ataggcagcg | cgcttatcaa | tatatctata | gaatgggcaa | agcataaaaa | cttgcatgga | 1260 |
| ctaatgcttg | aaacccagga | caataacctt | atagcttgta | aattctatca | taattgggta | 1320 |
| atgactccaa | cttattgata | gtgttttatg | ttcagataat | gcccgatgac | tttgtcatgc | 1380 |
| agctccaccg | attttgagaa | cgacagcgac | ttccgtccca | gccgtgccag | gtgctgcctc | 1440 |
| agattcaggt | tatgccgctc | aattcgctgc | gtatatcgct | tgctgattac | gtgcagcttt | 1500 |
| cccttcaggc | gggattcata | cagcggccag | ccatccgtca | tccatatcac | cacgtcaaag | 1560 |
| ggtgacagca | ggctcataag | acgccccagc | gtcgccatag | tgcgttcacc | gaatacgtgc | 1620 |
| gcaacaaccg | tcttccggag | actgtcatac | gcgtaaaaca | gccagcgctg | gcgcgattta | 1680 |
| gccccgacat | agccccactg | ttcgtccatt | tccgcgcaga | cgatgacgtc | actgcccggc | 1740 |
| tgtatgcgcg | aggttaccga | ctgcggcctg | agttttttaa | gtgacgtaaa | atcgtgttga | 1800 |
| ggccaacgcc | cataatgcgg | gctgttgccc | ggcatccaac | gccattcatg | gccatatcaa | 1860 |
| tgattttctg | gtgcgtaccg | ggttgagaag | cggtgtaagt | gaactgcagt | tgccatgttt | 1920 |
| tacggcagtg | agagcagaga | tagcgctgat | gtccggcggt | gcttttgccg | ttacgcacca | 1980 |
| ccccgtcagt | agctgaacag | gagggacagc | tgatagacac | agaagccact | ggagcacctc | 2040 |

```
aaaaacacca tcatacacta aatcagtaag ttggcagcat cacccataat tgtggtttca    2100
aaatcggctc cgtcgatact atgttatacg ccaactttga aaacaactttt gaaaaagctg   2160 ttttctggta tttaaggttt tagaatgcaa ggaacagtga attggagttc gtcttgttat    2220
aattagcttc ttggggtatc tttaaatact gtagaaaaga ggaaggaaat aataaatggc    2280
taaaatgaga atatcaccgg aattgaaaaa actgatcgaa aaataccgct gcgtaaaaga    2340
tacgaaagga atgtctcctg ctaaggtata taagctggtg ggagaaaatg aaaacctata    2400
tttaaaaatg acggacagcc ggtataaagg gaccacctat gatgtggaac gggaaaagga    2460
catgatgcta tggctggaag gaaagctgcc tgttccaaag gtcctgcact ttgaacggca    2520
tgatggctgg agcaatctgc tcatgagtga ggccgatggc gtcctttgct cggaagagta    2580
tgaagatgaa caaagccctg aaaagattat cgagctgtat gcggagtgca tcaggctctt    2640
tcactccatc gacatatcgg attgtcccta tacgaatagc ttagacagcc gcttagccga    2700
attggattac ttactgaata acgatctggc cgatgtggat tgcgaaaact gggaagaaga    2760 cactccatttt aaagatccgc gcgagctgta tgattttttta aagacggaaa agcccgaaga   2820
ggaacttgtc ttttcccacg gcgacctggg agacagcaac atctttgtga agatggcaa     2880 agtaagtggc tttattgatc ttgggagaag cggcagggcg gacaagtggt atgacattgc    2940
cttctgcgtc cggtcgatca gggaggatat cggggaagaa cagtatgtcg agctatttt     3000 tgacttactg gggatcaagc ctgattggga gaaaataaaa tattatattt tactggatga    3060 attgtttttag tacctagatg tggcgcaacg atgccggcga caagcaggag cgcaccgact   3120
tcttccgcat caagtgtttt ggctctcagg ccgaggccca cggcaagtat ttgggcaagg    3180
ggtcgctggt attcgtgcag ggcaagattc ggaataccaa gtacgagaag gacggccaga    3240
cggtctacgg gaccgacttc attgccgata aggtggatta tctggacacc aaggcaccag    3300
gcgggtcaaa tcaggaataa gggcacattg ccccggcgtg agtcgggca atcccgcaag    3360 gagggtgaat gaatcggacg tttgaccgga aggcatacag gcaagaactg atcgacgcgg    3420
ggttttccgc cgaggatgcc gaaaccatcg caagccgcac cgtcatgcgt gcgccccgcg    3480
aaaccttcca gtccgtcggc tcgatggtcc agcaagctac ggccaagatc gagcgcgaca    3540
gcgtgcaact ggctccccct gccctgcccg cgccatcggc cgccgtggag cgttcgcgtc    3600
gtctcgaaca ggaggcggca ggtttggcga agtcgatgac catcgacacg cgaggaacta    3660
tgacgaccaa gaagcgaaaa accgccggcg aggacctggc aaaacaggtc agcgaggcca    3720
agcaggccgc gttgctgaaa cacacgaagc agcagatcaa ggaaatgcag ctttccttgt    3780
tcgatattgc gccgtggccg gacacgatgc gagcgatgcc aaacgacacg gcccgctctg    3840
ccctgttcac cacgcgcaac aagaaaatcc gcgcgaggc gctgcaaaac aaggtcattt     3900
tccacgtcaa caaggacgtg aagatcacct acaccggcgt cgagctgcgg ccgacgatg     3960 acgaactggt gtggcagcag gtgttggagt acgcgaagcg cacccctatc ggcgagccga    4020
tcaccttcac gttctacgag cttttgccagg acctgggctg gtcgatcaat ggccggtatt   4080
acacgaaggc cgaggaatgc ctgtcgcgcc tacaggcgac ggcgatgggc ttcacgtccg    4140
accgcgttgg gcacctggaa tcggtgtcgc tgctgcaccg cttccgcgtc ctggaccgtg    4200
gcaagaaaac gtcccgttgc caggtcctga tcgacgagga aatcgtcgtg ctgtttgctg    4260
gcgaccacta cacgaaattc atatgggaga agtaccgcaa gctgtcgccg acggcccgac    4320
ggatgttcga ctatttcagc tcgcaccggg agccgtaccc gctcaagctg gaaaccttcc    4380
```

-continued

```
gcctcatgtg cggatcggat ccacccgcg tgaagaagtg gcgcgagcag gtcggcgaag    4440
cctgcgaaga gttgcgaggc agcggcctgg tggaacacgc ctgggtcaat gatgacctgg    4500
tgcattgcaa acgctagggc cttgtggggt cagttccggc tggggttca gcagccagcg     4560 ctttactggc atttcaggaa caagcgggca ctgctcgacg cacttgcttc gctcagtatc    4620
gctcgggacg cacggcgcgc tctacgaact gccgataaac agaggattaa aattgacaat    4680
tgtgattaag gctcagattc gacggcttgg agcggccgac gtgcaggatt ccgcgagat    4740 ccgattgtcg gccctgaaga aagctccaga gatgttcggg tccgtttacg agcacgagga    4800
gaaaaagccc atggaggcgt tcgctgaacg gttgcgagat gccgtggcat tcggcgccta    4860
catcgacggc gagatcattg gctgtcggt cttcaaacag gaggacggcc ccaaggacgc     4920
tcacaaggcg catctgtccg gcgttttcgt ggagcccgaa cagcgaggcc gaggggtcgc    4980
cggtatgctg ctgcgggcgt tgccggcggg tttattgctc gtgatgatcg tccgacagat    5040
tccaacggga atctggtgga tgcgcatctt catcctcggc gcacttaata tttcgctatt    5100
ctggagcttg ttgtttattt cggtctaccg cctgccgggc ggggtcgcgg cgacggtagg    5160
cgctgtgcag ccgctgatgg tcgtgttcat ctctgccgct ctgctaggta gcccgatacg    5220
attgatggcg gtcctggggg ctatttgcgg aactgcgggc gtggcgctgt tggtgttgac    5280
accaaacgca gcgctagatc ctgtcggcgt cgcagcgggc ctggcggggg cggtttccat    5340
ggcgttcgga accgtgctga cccgcaagtg caacctccc gtgcctctgc tcacctttac     5400
cgcctggcaa ctggcggccg gaggacttct gctcgttcca gtagctttag tgtttgatcc    5460
gccaatcccg atgcctacag gaaccaatgt tctcggcctg gcgtggctcg gcctgatcgg    5520
agcgggttta acctacttcc tttggttccg ggggatctcg cgactcgaac ctacagttgt    5580
ttccttactg ggctttctca gccccagatc tgggtcgat cagccgggga tgcatcaggc     5640
cgacagtcgg aacttcgggt ccccgacctg taccattcgg tgagcaatgg atagggagt     5700 tgatatcgtc aacgttcact tctaaagaaa tagcgccact cagcttcctc agcggcttta    5760
tccagcgatt tcctattatg tcggcatagt tctcaagatc gacagcctgt cacggttaag    5820
cgagaaatga ataagaaggc tgataattcg gatctctgcg agggagatga tatttgatca    5880
caggcagcaa cgctctgtca tcgttacaat caacatgcta ccctccgcga gatcatccgt    5940
gtttcaaacc cggcagctta gttgccgttc ttccgaatag catcggtaac atgagcaaag    6000
tctgccgcct tacaacggct ctcccgctga cgccgtcccg gactgatggg ctgcctgtat    6060
cgagtggtga ttttgtgccg agctgccggt cggggagctg ttggctggct ggtggcagga    6120
tatattgtgg tgtaaacaaa ttgacgctta gacaacttaa taacacattg cggacgtttt    6180
taatgtactg gggtggtttt tcttttcacc agtgagacgg gcaacagctg attatcgatg    6240
aattcgacgt taactgatat tgaaggagca ttttttgggc ttggctggag ctagtggagg    6300
tcaacaatga atgcctattt tggtttagtc gtccaggcgg tgagcacaaa atttgtgtcg    6360
tttgacaaga tggttcattt aggcaactgg tcagatcagc cccacttgta gcagtagcgg    6420
cggcgctcga agtgtgactc ttattagcag acaggaacga ggacattatt atcatctgct    6480
gcttggtgca cgataacttg gtgcgtttgt caagcaaggt aagtggacga cccggtcata    6540
ccttcttaag ttcgcccttc ctcccttat ttcagattca atctgactta cctattctac      6600
ccaagcatcc aaatgaaaaa gcctgaactc accgcgacgt ctgtcgagaa gtttctgatc    6660
gaaaagttcg acacgtctc cgacctgatg cagctcgcgg agggcgaaga atctcgtgct    6720
ttcagcttcg atgtaggagg gcgtggatat gtcctgcggg taaatagctg cgccgatggt    6780
```

```
ttctacaaag atcgttatgt ttatcggcac tttgcatcgg ccgcgctccc gattccggaa    6840
gtgcttgaca ttggggagtt cagcgagagc ctgacctatt gcatctcccg ccgtgcacag    6900
ggtgtcacgt tgcaagacct gcctgaaacc gaactgcccg ctgttctcca gccggtcgcg    6960
gaggccatgg atgcgatcgc tgcggccgat cttagccaga cgagcgggtt cggcccattc    7020
ggaccgcaag gaatcggtca atacactaca tggcgtgatt tcatatgcgc gattgctgat    7080
ccccatgtgt atcactggca aactgtgatg gacgacaccg tcagtgcgtc cgtcgcgcag    7140
gctctcgatg agctgatgct ttgggccgag gactgccccg aagtccggca cctcgtgcac    7200
gcggatttcg gctccaacaa tgtcctgacg gacaatggcc gcataacagc ggtcattgac    7260
tggagcgagg cgatgttcgg ggattcccaa tacgaggtcg ccaacatctt cttctggagg    7320
ccgtggttgg cttgtatgga gcagcagacg cgctacttcg agcggaggca tccggagctt    7380
gcaggatcgc cgcggctccg ggcgtatatg ctccgcattg gtcttgacca actctatcag    7440
agcttggttg acggcaattt cgatgatgca gcttgggcgc agggtcgatg cgacgcaatc    7500
gtccgatccg gagccgggac tgtcgggcgt acacaaatcg cccgcagaag cgcggccgtc    7560
tggaccgatg gctgtgtaga agtactcgcc gatagtggaa accgacgccc cagcactcgt    7620
ccgagggcaa aggaatagag tagatgccga ccgggaacca gttaacgtct agaggtcata    7680
acgtgactcc cttaattctc cgctcatgat cagattgtcg tttcccgcct tcagtttaaa    7740
ctatcagtgt ttgacaggat atattggcgg gtaaacctaa gagaaaagag cgtttattag    7800
aataatcgga tatttaaaag ggcgtgaaaa ggtttatccg ttcgtccatt tgtatgtgca    7860
tgccaaccac agggttcccc agatctggcg ccggccagcg agacgagcaa gattggcgtc    7920
gagctgtcag accaagttta ctcatatata ctttagattg atttaaaact tcattttttaa   7980 tttaaaagga tctaggtgaa gatcctttt gataatctca tgaccaaaat cccttaacgt    8040
gagttttcgt tccactgagc gtcagacccc gtagaaaaga tcaaaggatc ttcttgagat    8100 ccttttttc tgcgcgtaat ctgctgcttg caaacaaaaa aaccaccgct accagcggtg    8160
gtttgtttgc cggatcaaga gctaccaact cttttccga aggtaactgg cttcagcaga    8220
gcgcagatac caaatactgt ccttctagtg tagccgtagt taggccacca cttcaagaac    8280
tctgtagcac cgcctacata cctcgctctg ctaatcctgt taccagtggc tgctgccagt    8340
ggcgataagt cgtgtcttac cgggttggac tcaagacgat agttaccgga taaggcgcag    8400
cggtcgggct gaacgggggg ttcgtgcaca gcccagct tggagcgaac gacctacacc    8460
gaactgagat acctacagcg tgagctatga gaaagcgcca cgcttcccga agggagaaag    8520
gcggacaggt atccggtaag cggcagggtc ggaacaggag agcgcacgag ggagcttcca    8580
gggggaaacg cctggtatct ttatagtcct gtcgggtttc gccacctctg acttgagcgt    8640
cgatttttgt gatgctcgtc agggggggcgg agcctatgga aaaacgccag caacgcggcc    8700 ttttttacggtt cctggccttt tgctggcctt tgctcaca tgttctttcc tgcgttatcc   8760
cctgattctg tggataaccg tattaccgcc tttgagtgag ctgataccgc tcgccgcagc    8820
cgaacgaccg agcgcagcga gtcagtgagc gaggaagcgg aagactcgac gcgcttttcc    8880
gctgcataac cctgcttcgg ggtcattata gcgattttt cggtatatcc atcctttttc    8940
gcacgatata caggattttg ccaaagggtt cgtgtagact ttccttggtg tatccaacgg    9000
cgtcagccgg gcaggatagg tgaagtaggc ccacccgcga gcgggtgttc cttcttcact    9060
gtcccttatt cgcacctggc ggtgctcaac gggaatcctg ctctgcgagg ctggccggct    9120
```

```
accgccggcg taacagatga gggcaagcgg atggctgatg aaaccaagcc aaccaggaag    9180
ggcagcccac ctatcaaggt gtactgcctt ccagacgaac gaagagcgat tgaggaaaag    9240
gcggcggcgg ccggcatgag cctgtcggcc tacctgctgg ccgtcggcca gggctacaaa    9300
atcacgggcg tcgtggacta tgagcacgtc cgcgagctgg cccgcatcaa tggcgacctg    9360
ggccgcctgg gcggcctgct gaaactctgg ctcaccgacg acccgcgcac ggcgcggttc    9420
ggtgatgcca cgatcctcgc cctgctggcg aagatcgaag agaagcagga cgagcttggc    9480
aaggtcatga tgggcgtggt ccgcccgagg gcagagccat gactttttta gccgctaaaa    9540
cggccggggg gtgcgcgtga ttgccaagca cgtccccatg cgctccatca agaagagcga    9600
cttcgcggag ctggtgaagt acatcaccga cgagcaaggc aagaccgagc gcctttgcga    9660
cgctca                                                               9666

<210> SEQ ID NO 2
<211> LENGTH: 654
<212> TYPE: DNA
<213> ORGANISM: Mortierella formosensis

<400> SEQUENCE: 2
atggccatca aggaatacca gcgcgagttc attgagtttg ccatcaagaa cgaggtcttg     60
aagttcggag agttcaccct caagtccggc cgtatctcgc cctacttctt gaacgcgggc    120
cttttcaaca ctggcgcctc gctctccaag atcggaaagt tctacgccgc tgccgtcagc    180
gattcgggca ttgagcacga catcatcttt ggccccgcct acaagggtgt ccctctggcc    240
tgcaccaccg tcattgcctt ggccgaggcc cctacaacag gacacgcc ctactgcttc      300
aaccgcaagg agaagaagga ccatggtgag ggcggcacga ttgttggatc agcactgaag    360
ggcaaggtcc tggtcattga cgatgttatc accgccggca ccgccatccg cgagtctgtc    420
cagatcattg aggactgcaa ggcccaattg ctggtgtttt ggtcgcggt ggatcgtcag     480
gagactggca agaacggcga catgtctgct atccaggagg tcgagagaga ctttggtgtc    540
cctgtcaagg ccattgtgac catgacccac atcatgcagt acatggagga aagggaacc     600
tatggcgagc acttgaccca gatgcgcgct taccgggaga agtacggtgt ttag          654

<210> SEQ ID NO 3
<211> LENGTH: 1393
<212> TYPE: DNA
<213> ORGANISM: Mortierella formosensis

<400> SEQUENCE: 3
cgacgctgac attacacatt tatccgttcg ccgatataga cttaaatggg acgaggagaa     60
cttgatcatc acagaggctc agaaggattc gacaatgaaa attgatgagc caagacgcc    120
ctatgttcac tacgaccacg agctggacaa agtgatcgat atgaatggta actgaaaaca    180
tggacatcca gagatcttga gcacccacga cgagatacac agaaagtcat caggcatact    240
gacacgtcct tcacgtcacg catttctgaa tttttttaatt tgtctagggg aaaccttctc    300
gttagacggg ggcaagacaa agcatgcttc tctagcccat ggtcagcctg taccatcgca    360
catgatgaa ccaatcggcg aggaagacga cgagagcgag gacgaagacg aggatgaaga    420
tggaccagac gagtcggggg attcagacga gggcgaggat gaagacgcaa agaagagtc     480
gcctcactaa aaaagtaagt tttctctatc tcattgcttc tttggttgct cggataatgc    540
ttagctgttg ttggtaaact cccagtagcc aacgctcatc atttgcaatt tttatttcg     600
catatatcag ttgaccacga caagtttgcc aagatgcgtg cggaacacta caagatgaag    660
```

| | |
|---|---|
| gaggcgcttc aattggggca tgagctggca gaggaagagc tgagtgcgct ggacagtcct | 720 |
| gatccaaacg atatgccagt gccgccatta ccgtcgtttg ctcaacagtc gaacgcggct | 780 |
| aggctgtcac gggaggctgg atcgaacaag ctgaaggagg accttgaaaa catggagctt | 840 |
| tagaggtttg gagttggctt tgaccatggc tatggctacg tattctgaac gacataaagg | 900 |
| acgctcattt ttcgctgcag gacattttt gagttgcagc acagaggggc aaggcggtgc | 960 |
| tctggactgc tttatcgggc tgctacgcgt gcgatttgtt tacgttttt ccggtttgtt | 1020 |
| ggccagcagt atttgtaggc cctgcagctg ggggtgggtt gatcctcttt ctcttctctt | 1080 |
| ctcttttctc ttttccctc ttctgatgtg tctcccaccc cacaaccttc tcctctgccc | 1140 |
| ccagccgcat cggtcccacc gccgcaaccc atcagcacac catggccatc aaggaatacc | 1200 |
| agcgcgagtt cattgagttt gccatcaaga acgaggtctt gaagttcgga gagttcaccc | 1260 |
| tcaagtccgg ccgtatctcg ccctacttct tgaacgcggg ccttttcaac actggcgcct | 1320 |
| cgctctccaa gatcggaaag ttctacgccg ctgccgtcag cgattcgggc attgagcacg | 1380 |
| acatcatctt tgg | 1393 |

<210> SEQ ID NO 4
<211> LENGTH: 1362
<212> TYPE: DNA
<213> ORGANISM: Mortierella formosensis

<400> SEQUENCE: 4

| | |
|---|---|
| ccctctggcc tgcaccaccg tcattgcctt ggccgaggcc ccctacaaca aggacacgcc | 60 |
| ctactgcttc aaccgcaagg agaagaagga ccatggtgag ggcggcacga ttgttggatc | 120 |
| agcactgaag ggcaaggtcc tggtcattga cgatgttatc accgccggca ccgccatccg | 180 |
| cgagtctgtc cagatcattg aggactgcaa ggcccaattg gctggtgttt tggtcgcggt | 240 |
| ggatcgtcag gagactggca gaacggcga catgtctgct atccaggagg tcgagagaga | 300 |
| cttggtgtc cctgtcaagg ccattgtgac catgacccac atcatgcagt acatggagga | 360 |
| gaagggaacc tatggcgagc acttgaccca gatgcgcgct taccgggaga agtacggtgt | 420 |
| ttagagcaag cgaactctgg atgggatgaa gctcggtttc aatgcggcga gcgagggctc | 480 |
| tgttggattt ttctcgtaat gcggggagac ggacgcccgg ggaacgatgt gctcctgatc | 540 |
| agtggttttc gagtgttctc gggacagccc gtcttgggaa accaccgaac gatggctatt | 600 |
| aataataaat acccatacaa caacttttcc tcagtgtggt agttggggtg tgatatcgcc | 660 |
| gtgcatgtcc aaggcttcag ctgcgcctgg cgacgagatg gaaggtcgtg ggaaagaggc | 720 |
| gtcgaaactg agctgtcaag aagaaagtaa aaaaaccgtc gtaaaataga gctgtgtcgt | 780 |
| caaatggcgt gtatggggta ttcggcgcga caggctattt gattccgatg gggctccaga | 840 |
| caaggcgcca ggagctcatc caagtcgatc gcccgctgta cgacgcctct gtagtatggg | 900 |
| gacatgattc tgctggtgga tgtttctgca gccaccagaa aattgaagct cagcctgtaa | 960 |
| aaaaaaatat tacattgtgg cgagcgagtc acttctctgt tctccttttc atttccaccc | 1020 |
| accctcattc cacatccatt caccaccgct cattcgcttc acaatggcag agactcttac | 1080 |
| tcaccctctt gtccaggacg gctggttcaa ggagaccggc accctctggc ccggccaggc | 1140 |
| catgactctc gaggtcaagg agattctgca cgttgaaaag tcgctcttcc aggacgtgct | 1200 |
| cgtcttccag tccacctcct acggcaacgt cctcgtcctc gacggcgtca tccaggccac | 1260 |
| cgagcgcgat gagttctcgt aagtgcgcta gtgtgctagt gtgtgctcga gctcctcacc | 1320 |

```
tggagtcctc tacctgatca ttccatatct gtgattcgca tg                        1362

<210> SEQ ID NO 5
<211> LENGTH: 36
<212> TYPE: DNA
<213> ORGANISM: Artificial Sequence
<220> FEATURE:
<223> OTHER INFORMATION: The sequence is synthesized

<400> SEQUENCE: 5
gaccggaatt ccgacgctga cattacacat ttatcc                                36

<210> SEQ ID NO 6
<211> LENGTH: 47
<212> TYPE: DNA
<213> ORGANISM: Artificial Sequence
<220> FEATURE:
<223> OTHER INFORMATION: The sequence is synthesized

<400> SEQUENCE: 6
tgacggtggt gcaggccaga gggccaaaga tgatgtcgtg ctcaatg                    47

<210> SEQ ID NO 7
<211> LENGTH: 47
<212> TYPE: DNA
<213> ORGANISM: Artificial Sequence
<220> FEATURE:
<223> OTHER INFORMATION: The sequence is synthesized

<400> SEQUENCE: 7
ttgagcacga catcatcttt ggccctctgg cctgcaccac cgtcatt                    47

<210> SEQ ID NO 8
<211> LENGTH: 31
<212> TYPE: DNA
<213> ORGANISM: Artificial Sequence
<220> FEATURE:
<223> OTHER INFORMATION: The sequence is synthesized

<400> SEQUENCE: 8
tgcggggtac ccatgcgaat cacagatatg g                                    31

<210> SEQ ID NO 9
<211> LENGTH: 35
<212> TYPE: DNA
<213> ORGANISM: Artificial Sequence
<220> FEATURE:
<223> OTHER INFORMATION: The sequence is synthesized

<400> SEQUENCE: 9
tttcgctagc acgacgttgt aaaacgacgg ccagt                                 35

<210> SEQ ID NO 10
<211> LENGTH: 34
<212> TYPE: DNA
<213> ORGANISM: Artificial Sequence
<220> FEATURE:
<223> OTHER INFORMATION: The sequence is synthesized

<400> SEQUENCE: 10
aacaacaatt ggggctccac cgcggtggcg gccg                                  34

<210> SEQ ID NO 11
<211> LENGTH: 25
<212> TYPE: DNA
<213> ORGANISM: Artificial Sequence
```

```
<220> FEATURE:
<223> OTHER INFORMATION: The sequence is synthesized

<400> SEQUENCE: 11
atgaccatca aggattacca gcgcg                                              25

<210> SEQ ID NO 12
<211> LENGTH: 25
<212> TYPE: DNA
<213> ORGANISM: Artificial Sequence
<220> FEATURE:
<223> OTHER INFORMATION: The sequence is synthesized

<400> SEQUENCE: 12
atccttaaac accgtacttc tcgcg                                              25
```